United States Patent [19]

Cummins

[11] 4,310,690

[45] Jan. 12, 1982

[54] PREPARATION OF THE CALCIUM SALT OF α-HYDROXY-GAMMA-METHYLMERCAPTOBUTYRIC ACID

[75] Inventor: Earl W. Cummins, Wilmington, Del.

[73] Assignee: E. I. Du Pont de Nemours and Company, Wilmington, Del.

[21] Appl. No.: 195,082

[22] Filed: Oct. 8, 1980

[51] Int. Cl.$^3$ ............................................. C07C 149/20
[52] U.S. Cl. ..................................................... 562/581
[58] Field of Search .......................................... 562/581

[56] References Cited

U.S. PATENT DOCUMENTS

| 2,938,053 | 5/1960 | Blake et al. | 562/581 |
| 3,534,095 | 10/1970 | Fingas | 562/581 |

FOREIGN PATENT DOCUMENTS

| 221492 | 5/1962 | Austria | 562/581 |
| 694592 | 9/1964 | Canada | 562/581 |
| 694650 | 9/1964 | Canada | 562/581 |
| 706430 | 3/1965 | Canada | 562/581 |
| 1157216 | 11/1963 | Fed. Rep. of Germany | 562/581 |

*Primary Examiner*—Paul J. Killos

[57] ABSTRACT

This invention relates to a novel process for preparing the calcium salt of α-hydroxy-γ-methylmercaptobutyric acid (MHBA).

5 Claims, 1 Drawing Figure

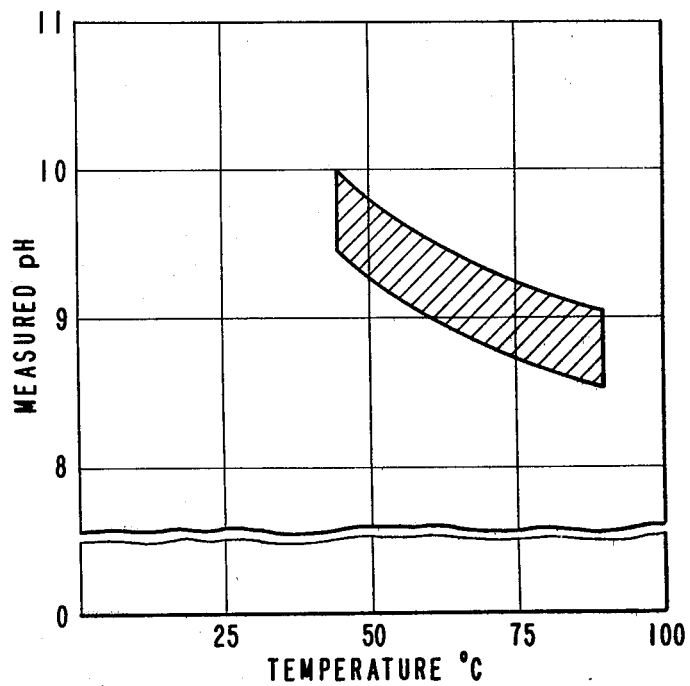

PREPARATION OF THE CALCIUM SALT OF α-HYDROXY-GAMMA-METHYLMERCAPTOBUTYRIC ACID

BACKGROUND OF THE INVENTION

The hydroxy analogue of methionine is a well-known chemical compound which is otherwise described as α-hydroxy-γ-methylmercaptobutyric acid (MHBA). This compound has nutrient values equivalent to the corresponding amino acid, methionine. The calcium salt of MHBA is also well-known, and it is usually in the form that it is used to fortify animal feeds.

Standard methods for preparing the calcium salt of α-hydroxy-γ-methylmercaptobutyric acid involve reacting an aqueous calcium hydroxide slurry with an aqueous solution of MHBA and ammonium sulfate. After first removing calcium sulfate by filtration, the product calcium salt is recovered from the solution by evaporative crystallization, followed by washing and drying. The evaporative crystallization step is energy-intensive, and this process is becoming increasingly disadvantageous as energy costs rise. Therefore, there is a clear need for a more economical and energy-efficient process for preparing this useful feed supplement.

SUMMARY OF THE INVENTION

A new process for preparing the calcium salt of α-hydroxy-γ-methylmercaptobutyric acid has now been found which eliminates the need for an evaporative crystallization step. This process comprises the following steps:

(a) contacting a reaction mixture obtained by hydrochloric acid hydrolysis of α-hydroxy-γ-methylmercapto butyronitrile to MHBA, with aqueous sodium hydroxide, recycled wash liquor from step (f) and water to form a solution having a pH in the range of about 6.0 to 8.0; the quantity of sodium hydroxide, recycled wash and water being controlled so as to provide a filtrate in step (d) with a sodium chloride content of about 18 to 22%;

(b) mixing into the solution formed in step (a) a quantity of aqueous lime slurry prepared using recycled wash liquor from step (f), said quantity being sufficient to form a reaction mixture having a pH of about 8.5 to 11.0 at about 45° to 90° C.;

(c) filtering the reaction mixture to recover the product calcium salt and to yield a filtrate having a sodium chloride content of about 18 to 22% by weight.

(d) washing the product calcium salt with water; and (e) retaining a portion of the wash liquor for recycling to the reaction mixture in step (a) and preparing the aqueous lime slurry used in step (b).

DETAILED DESCRIPTION OF THE INVENTION

The starting material in the process of this invention is a α-hydroxy-γ-methylmercaptobutyric acid (MHBA) hydrolyzate obtained by hydrolysis of α-hydroxy-γ-methylmercaptobutyronitrile with hydrochloric acid. This hydrolyzate may be prepared as described in U.S. Pat. No. 3,773,927, the disclosure of which is herein incorporated by reference.

The MHBA hydrolyzate, containing ammonium chloride solids, is contacted with aqueous sodium hydroxide, water and recycled wash liquor to form a solution having a pH of about 6.0 to 8.0, preferably about 6.5 to 7.0. The sodium hydroxide reacts with the ammonium chloride and any excess hydrogen chloride remaining from the preparation of the MHBA, forming sodium chloride. The concentration of the sodium hydroxide solution is not critical; however, a solution of about 50% NaOH is preferred.

In order to avoid the expensive evaporative crystallization step used heretofore, it is necessary to operate under conditions which reduce the solubility of the product calcium salt in the aqueous phase. This is done by controlling the sodium chloride concentration at a certain level. This decreases the solubility of the product calcium salt and thus insures isolation of the salt in economical yields. The product calcium salt is then easily recovered from the reaction mixture, a slurry, by filtration. If the sodium chloride content of the reaction mixture is not properly maintained, the product calcium salt either will be solubilized to an uneconomical level and must be recovered from solution in another step, for example, evaporative crystallization, or second phase sodium chloride will appear in the product calcium salt.

It has been found that an optimal sodium chloride concentration is one which will provide a sodium chloride content of about 18 to 22% by weight in the filtrate recovered on filtration of the final reaction mixture to yield the product calcium salt. This level of sodium chloride concentration reduces the loss of the product salt to the filtrate, but does not lead to excessive sodium chloride contamination of the product calcium salt. Therefore, the amount of water, sodium hydroxide and recycled wash liquor added to the MHBA hydrolyzate is controlled so as to insure the proper concentration of salt in the filtrate. An added proviso is that the concentration of sodium chloride in the reaction mass after neutralization with sodium hydroxide must not exceed about 16.5%. If higher concentrations are employed, second phase sodium chloride is present and a final product is obtained which contains excessive amounts of this material.

The solution of the ammonium salt of MHBA thus prepared is contacted with an aqueous lime slurry, prepared from recycled wash liquor, to form a slurry of the product calcium salt. The concentration of lime in the aqueous slurry will preferably be about 15 to 30%, more preferably about 25%. The determining factor in selecting the lime slurry concentration is that it result in a final filtrate containing 18 to 22% sodium chloride. The slurry is prepared by slaking lime with the recycled wash liquor described below.

It has been found advantageous for a batch process to add the lime slurry to the MHBA solution in two portions. First, a small amount of the lime is added, the amount being sufficient to commence nucleation of the product calcium salt in the reaction mixture. Once nucleation has occurred, the remainder of the lime slurry may be added to the reaction mixture. Following this method of addition results in a reaction mixture with a desirable, smooth consistency. In practice, it has been found that addition of approximately 8% of the total theoretical amount of lime to the MHBA solution is sufficient to commence nucleation of the product calcium salt. When the process of this invention is run continuously, the MHBA solution and the aqueous lime slurry will be added continuously to a reaction chamber already containing crystallized product calcium salt.

The temperature of the reaction mixture formed by combination of the MHBA solution and the aqueous lime slurry is maintained at about 45° to 90° C., preferably about 55° to 65° C., while the pH is maintained at about 8.5 to 11.0, preferably about 9.0 to 9.5. The graph in the drawing represents the optimal pH/temperature ranges. The temperature can be maintained within the desired range without external heating or cooling by controlling the temperature of the entering MHBA solution and lime slurry. The pH is maintained within the desired range by controlling the addition rates of the MHBA solution and the lime slurry.

The pH of the reaction mixture is conveniently measured with a glass and inverted glass sleeve silver/silver chloride electrode pair. The pH of the reaction mixture is maintained within the stated range to insure optimal product yields. Lower pH's result in loss of MHBA to the filtrate while higher values result in dilution of the final product with lime.

The product calcium salt can be recovered from the reaction mixture by filtration. The temperature of the reaction mixture is reduced to about 60°, if necessary, before filtration. The recovered product calcium salt is then washed and dried to yield a product preferably containing less than about one percent water.

In practice, it has been convenient to wash the product-calcium salt recovered on filtration of the reaction mixture with two substantially equal portions of water and to retain the second portion of wash liquor for recycling. The second wash liquor contains high concentrations of product calcium salt and low concentrations of sodium chloride relative to the filtrate, and recycling it produces increased product yields. The maximum yield is obtained by recycling any portion of wash liquor that contains a larger concentration of product calcium salt than the filtrate. The wash liquor can be recycled to the reaction mixture in step (a) of the process and used in preparing the lime slurry. The process can be operated without recycle, but the loss of calcium product salt to waste is excessive.

It is convenient and economical to operate the process of this invention in a continuous manner. In this modification, the slurry prepared as taught in U.S. Pat. No. 3,773,927, water, recycle filtrate and aqueous sodium hydroxide are brought together in a reaction vessel. The rates are controlled so that the average residence time is from 0.3 to 2.0 hours, preferably 0.5 to 1.0 hours. The rate of the sodium hydroxide addition is varied so that the pH is maintained at 6 to 8, preferably 6.5 to 7.0. The resulting solution along with the lime slurry is added continuously to a reaction chamber already containing a slurry of crystallized product calcium salt. Temperature and pH are maintained within the same parameters as in the batch process. The flow rates of the reactants are adjusted so that the average hold up time in the reaction chamber is 0.5 to 3.0 hours, preferably 1.0 to 2.0 hours. The slurry exiting the vessel if above 60° C., is cooled to this temperature and transferred to a moving bed filter, washed with water and a portion of the wash liquor recycled as described for the previously described batch process. The product exiting the filter is dried by conventional means.

The following examples illustrate the process of this invention. Unless otherwise specified, all parts are by weight and all temperatures are in degrees Centigrade.

EXAMPLE 1

A solution of α-hydroxy-γ-methylmercaptobutyric acid containing second phase ammonium chloride, prepared as described in Example 1 of U.S. Pat. No. 3,773,927, is mixed in the vessel in which it is prepared with 29 parts water and 46.7 parts recycle wash containing 8.7% sodium chloride and 6.0% product calcium salt. It is then reacted with 50% aqueous sodium hydroxide added through an addition funnel while the temperature of the mixture is maintained at 90° C. Addition is continued until the pH in the reaction mass reaches 6.5. In all, about 94 grams are required.

After cooling the resulting solution to 60° C., 10 parts of a 25% slurry of calcium hydroxide (made by slaking lime in recycle wash containing 8.7% sodium chloride and 6.0% product calcium salt) is added to the solution with a peristaltic pump equipped with 0.0315" Viton ® tubing (fluoroelastomer manufactured by E. I. du Pont de Nemours and Co.). When nucleation has occurred, the pump is started and lime addition is resumed. It is continued at the rate of 2.5 parts/minute until the pH of the mixture reaches 9.5 as measured by a glass electrode and inverted sleeve silver/silver chloride reference electrode. In all, about 131 parts of lime slurry are required.

It is beneficial to have good agitation during the lime addition and to add the lime slurry above the tip of the agitator blade. This aids the formation of discrete, large size particles. Poor agitation and addition near the side of the flask yields very fine particles and a viscous, difficult to stir, reaction mass.

The reaction mass is filtered through a coarse sintered glass funnel and washed with two portions of water to give wash liquors of 114 and 155 parts. The filtrate and first wash are discarded and the second wash, containing 8.7% sodium chloride and 6.0% product calcium salt, is recycled.

The residue is dried in a vacuum oven at 60° C. to give 167 parts of α-hydroxy-γ-methylmercaptobutyric acid, calcium salt (93% of theory when adjusted for the amount recycled and the amount in the wash intended for recycle) having a purity of 94% and containing 4% sodium chloride.

The recycle streams are adjusted to maintain the concentration of salt in the filtrate at 18 to 22%. This is accomplished by determining the concentration of salt in the recycle stream, using the amount necessary to prepare the lime slurry and adding the remainder to the MHBA reaction mass. The amount of water required to be added to the MHBA was calculated by use of the following equation:

$$W = .216F + \frac{C(S-8.7)}{25} - R\left(1 - \frac{S}{20}\right)$$

where
W = parts of water required;
F = parts of hydrolyzate;
C = parts of recycle used for lime slaking;
R = parts of recycle to hydrolyzate; and
S = % salt in recycle.

EXAMPLE 2

A solution of α-hydroxy-γ-methylmercaptobutyric acid containing a second phase of ammonium chloride, prepared as described in Example 1 of U.S. Pat. No. 3,773,927, is diluted with 36.4 parts of water and 46.7 parts recycle wash liquor containing 8% sodium chloride. The resulting solution is added to a glass vessel containing a slurry of product calcium salt, as prepared in Example 1, simultaneously with 50% aqueous sodium hydroxide. The temperature is maintained at 90° C. by external heating or cooling, as required, and the pH is maintained at 6.7±0.2 by varying the flow of sodium hydroxide. The average residence time is one-half hour.

The resulting solution is added to a vessel equipped with an agitator. Simultaneously, a 25% slurry of calcium hydroxide (prepared by slaking lime in recycle liquor containing 8% sodium chloride) is added to the vessel at a rate such that the pH, as measured with a glass electrode and inverted sleeve silver/silver chloride reference electrode, is maintained at 9.0–9.5. The temperature of the mixture is maintained at ~60° C. by external cooling or heating as required. The flow rate of the streams are adjusted so that the average residence time is one hour.

The overflow from this vessel is deposited on a straight line continuous moving filter bed and is washed with water. The wash water is controlled so that 204 parts of wash are obtained per hour. The first portion of wash coming off the filter, 42% of the total, is sent to waste treatment along with the filtrate. The second portion of the wash is recycled back to prepare the lime slurry and dilute the original reaction mass.

The product exiting the filter is dried in a rotary drum drier to yield a 95% pure product containing 4% salt. Over an extended period, the recovery of product calcium salt is 93%, the remaining 7% being lost in the filtrate and wash liquor.

The second portion of wash liquor was recycled for use in preparing the lime slurry. The unused portion was recycled for addition to the MHBA solution. The amount of dilution water needed to maintain the salt content of the filtrate at 20% was calculated according to the following equation:

$$W = .216F + \frac{C(S-8.7)}{25} - R\left(1 - \frac{S}{20}\right)$$

where

W = flow rate of water addition in parts/hour;
F = flow rate of MHBA solution in parts/hour;
C = flow rate of recycle to lime slaker in parts/hours;
R = flow rate of recycle to neutralizer in parts/hours; and
S = % salt in recycle.

What is claimed is:

1. A process for preparing the calcium salt of α-hydroxy-γ-methylmercaptobutyric acid (MHBA) which comprises:
   (a) contacting a reaction mixture obtained by hydrochloric acid hydrolysis of α-hydroxy-γ-methylmercapto butyronitrile to MHBA with aqueous sodium hydroxide, recycled wash liquor from step (f) and water to form a solution having a pH in the range of about 6.0 to 8.0; the quantity of sodium hydroxide, recycled wash and water being controlled so as to provide a filtrate in step (d) with a sodium chloride content of about 18 to 22%;
   (b) mixing into the solution formed in step (a) a quantity of aqueous lime slurry prepared using recycled wash liquor from step (f), said quantity being sufficient to form a reaction mixture having a pH of about 8.5 to 11.0 at about 45° to 90° C.;
   (c) filtering the reaction mixture to recover the product calcium salt and to yield a filtrate having a sodium chloride content of about 18 to 22% by weight;
   (d) washing the product calcium salt with water; and
   (e) retaining a portion of the wash liquor for recycling to the reaction mixture in step (a) and preparing the aqueous lime slurry used in step (b).

2. The process of claim 1 wherein the solution formed in step (a) has a pH in the range of about 6.5 to 7.0.

3. The process of claim 1 wherein the temperature of the reaction mixture in step (b) is maintained at about 50° to 60° C.

4. The process of claim 1 wherein the pH of the reaction mixture in step (b) is about 9.0 ;1 to 9.5.

5. The process of claim 1 wherein the product calcium salt is dried to reduce water content to at least about 1% by weight.

* * * * *

UNITED STATES PATENT OFFICE
CERTIFICATE OF CORRECTION

PATENT NO. : 4,310,690
DATED : January 12, 1982
INVENTOR(S) : Earl W. Cummins

It is certified that error appears in the above-identified patent and that said Letters Patent are hereby corrected as shown below:

In the Claims:

Claim 4 - Column 6, line 39

Please replace "9.0 ;1 to 9.5." with
-- 9.0 to 9.5. --

Signed and Sealed this

Sixth Day of April 1982

|SEAL|

Attest:

GERALD J. MOSSINGHOFF

Attesting Officer    Commissioner of Patents and Trademarks